United States Patent
Baba

(10) Patent No.: US 8,538,118 B2
(45) Date of Patent: Sep. 17, 2013

(54) METHOD OF REMOVING MOIRÉ IN FLUOROSCOPIC X-RAY IMAGE AND X-RAY IMAGING EQUIPMENT USING THE SAME

(75) Inventor: Shingo Baba, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 269 days.

(21) Appl. No.: 12/988,457

(22) PCT Filed: Jan. 22, 2009

(86) PCT No.: PCT/JP2009/000233
§ 371 (c)(1),
(2), (4) Date: Oct. 18, 2010

(87) PCT Pub. No.: WO2009/130829
PCT Pub. Date: Oct. 29, 2009

(65) Prior Publication Data
US 2011/0038522 A1    Feb. 17, 2011

(30) Foreign Application Priority Data
Apr. 22, 2008 (JP) ................................. 2008-111658

(51) Int. Cl.
*G06K 9/00*   (2006.01)
*G06K 9/40*   (2006.01)

(52) U.S. Cl.
USPC .......................................... 382/132; 382/275

(58) Field of Classification Search
USPC ........................................................ 382/132
See application file for complete search history.

(56) References Cited

U.S. PATENT DOCUMENTS

| 5,513,016 A * | 4/1996 | Inoue | 358/3.26 |
| 6,614,044 B2 * | 9/2003 | Yamada | 250/584 |
| 7,826,682 B2 * | 11/2010 | Behiels et al. | 382/275 |
| 2002/0196985 A1 * | 12/2002 | Sasada | 382/269 |
| 2003/0002747 A1 * | 1/2003 | Zaklika et al. | 382/260 |
| 2003/0016854 A1 * | 1/2003 | Inoue et al. | 382/132 |

FOREIGN PATENT DOCUMENTS
JP    2002-330341 A    11/2002

OTHER PUBLICATIONS

Guerra Filho, Gutemberg, Matlab—Image Processing Tutorial, Mar. 2002, Department of Computer Science—University of Maryland (www.cs.umd.edu/class/spring2002/cmsc426/matlab.ppt), pp. 1-43 (see p. 43 for publication date).*

* cited by examiner

*Primary Examiner* — Utpal Shah
(74) *Attorney, Agent, or Firm* — Cheng Law Group, PLLC

(57) ABSTRACT

Provided is a method of removing a moiré in a fluoroscopic X-ray image that preliminarily complements a defective pixel with no disturbance in regularity of a moiré pattern to ensure that no trace of the defective pixel and no ghost thereof create even when the fluoroscopic X-ray image contains the defective pixel. A moiré frequency derivation section determines frequency of the moiré that appears in the fluoroscopic X-ray image, a defective pixel preliminary complement section forms a preliminary complement image, a moiré removal section conducts frequency analysis of the preliminary complement image to form a moiré removed image, an image smoothing section performs an image smoothing process to the preliminary complement image to form a smoothed image suitable for complement of the defective pixel, and a first defective pixel recomplement section recomplements the defective pixel by superimposing the moiré removed image on the smoothed image.

6 Claims, 11 Drawing Sheets

Fig. 3
(a)
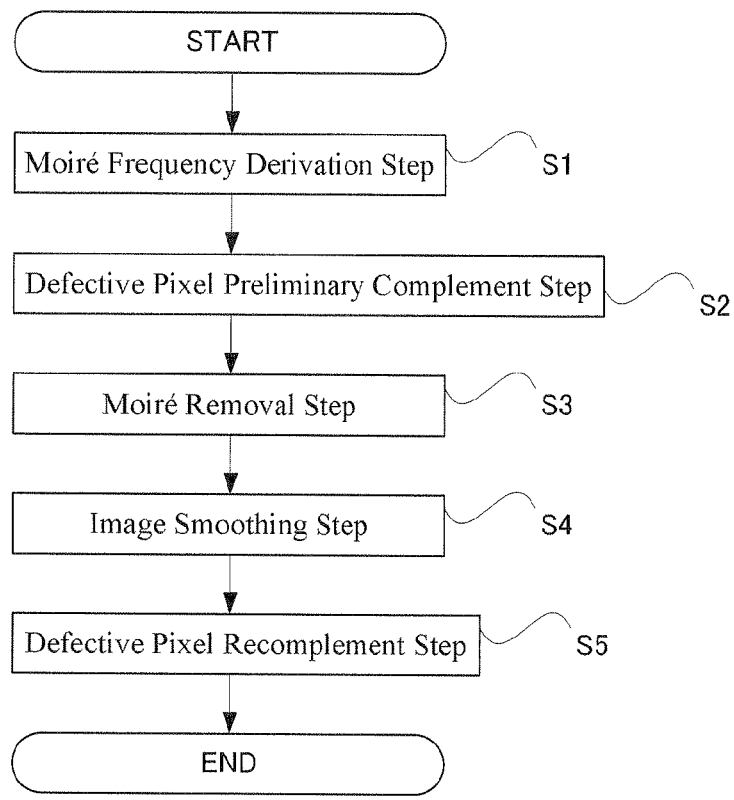
(b)
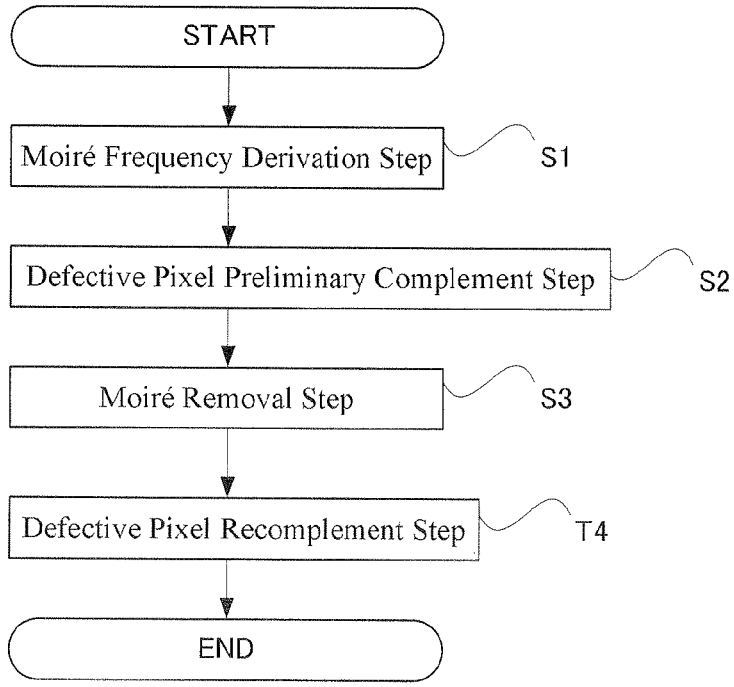

Fig.4
(a)
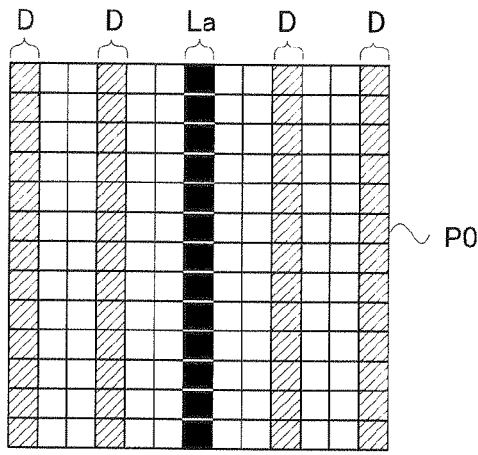
P0
(b)
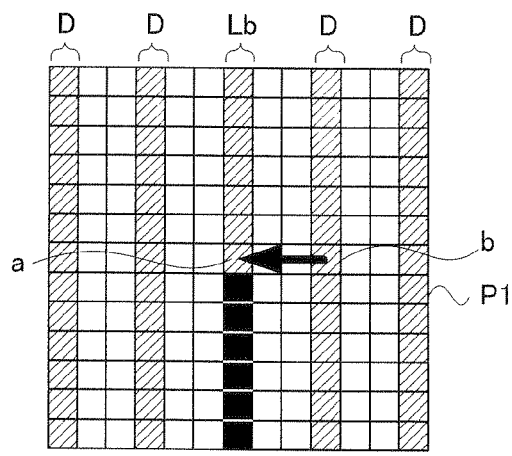
P1
(c)
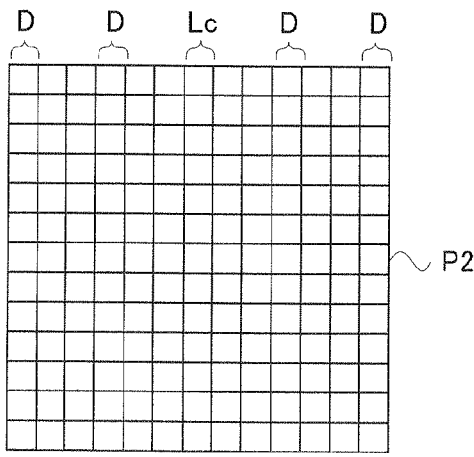
P2

Fig. 7
(a)
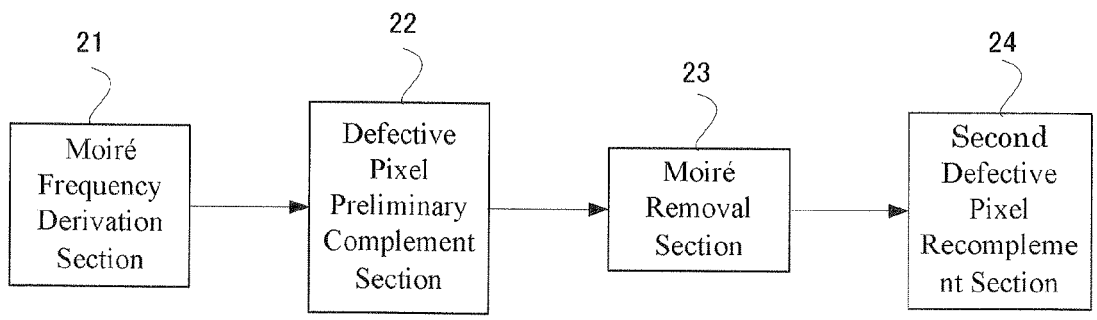
(b)
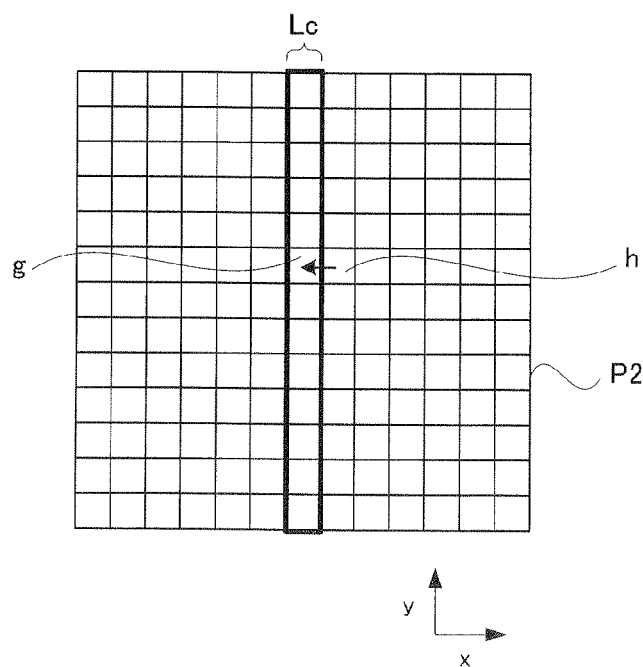

Fig. 9
(a)
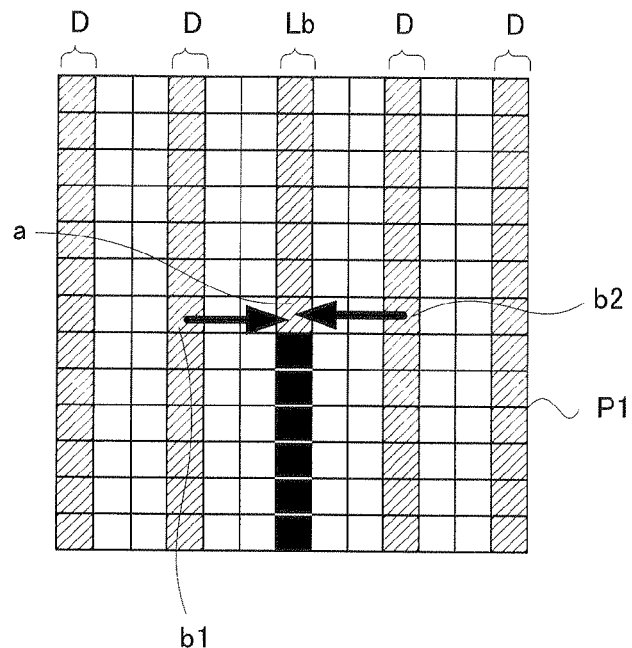
(b)
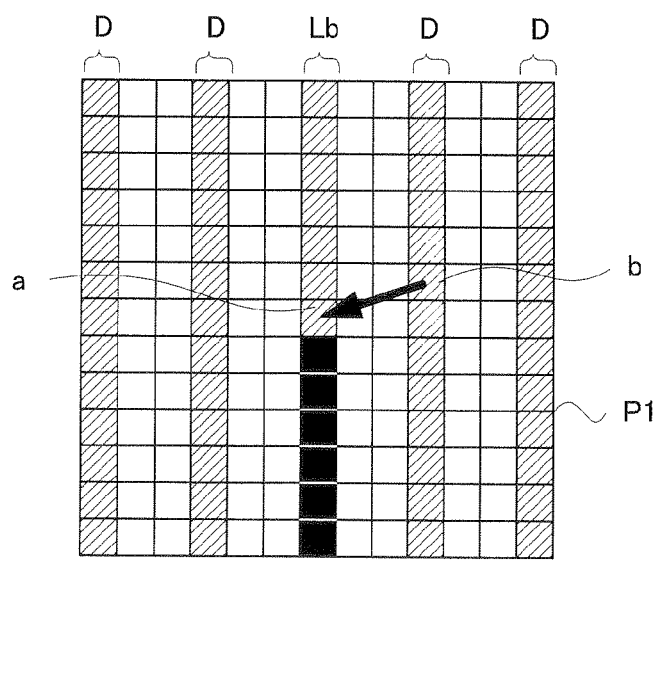

Fig.10
(a) Prior Art
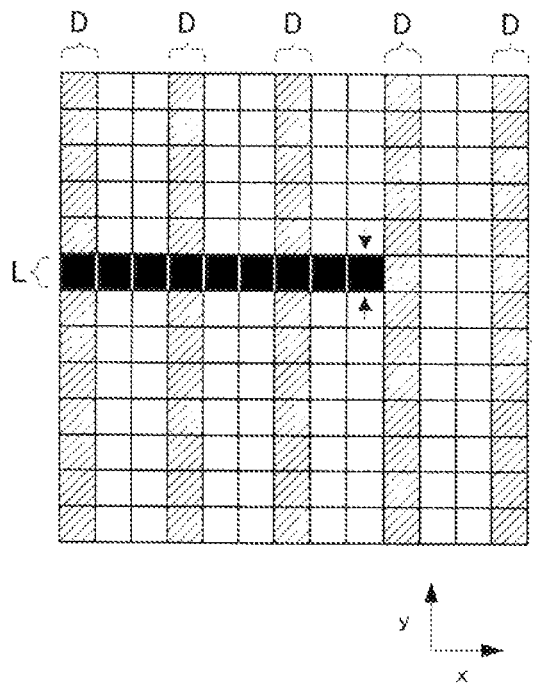
(b) Prior Art
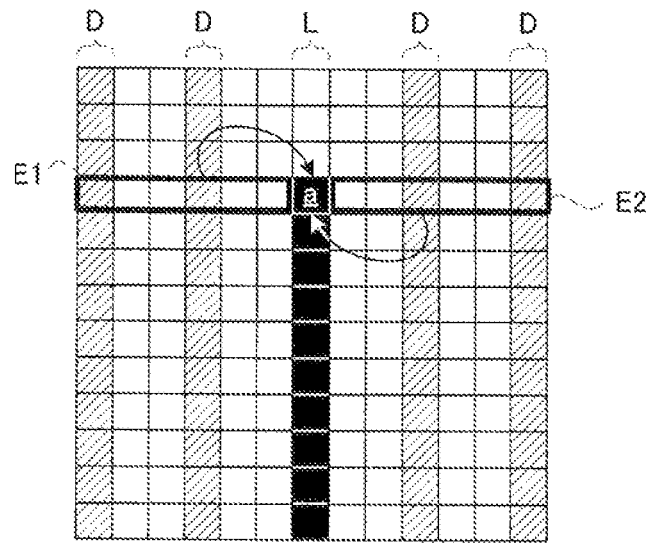

Fig. 11
(a) Prior Art
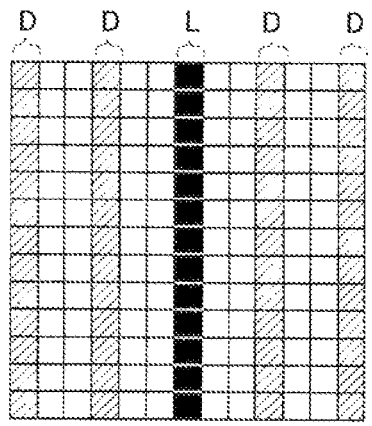
(b) Prior Art
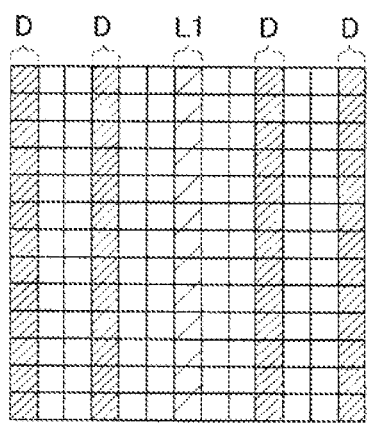
(c) Prior Art
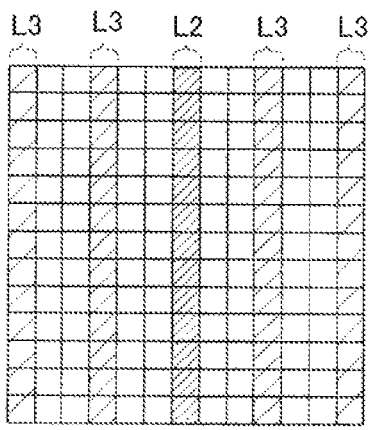

US 8,538,118 B2

METHOD OF REMOVING MOIRÉ IN FLUOROSCOPIC X-RAY IMAGE AND X-RAY IMAGING EQUIPMENT USING THE SAME

TECHNICAL FIELD

This invention relates to a method of removing a moiré that occurs from interference between an arrangement pattern of an X-ray grid and an arrangement pattern of detecting elements in an FPD to appear in a fluoroscopic X-ray image and to X-ray equipment using thereof. More particularly, this invention relates to a technique of removing a moiré containing a defective pixel that appears in the fluoroscopic X-ray image.

BACKGROUND ART

Examples of X-ray imaging equipment to take a fluoroscopic X-ray image of a subject includes one having an X-ray source that emits X-ray beams in a cone shape and a flat panel detecting element (abbreviated as "FPD") that detects them. The FPD has an X-ray detection surface where the X-ray detecting elements are arranged in two dimensions.

X-rays emitted from the X-ray source are once scattered in the subject, and then enter into the FPD. The scattered X-rays entering into the FPD lead to a lower contrast fluoroscopic X-ray image. To avoid incidence of such the scattered X-rays into the FPD, a sheet-like X-ray grid having strip metallic foils arranged therein is provided in the X-ray imaging equipment so as to cover the X-ray detection surface of the FPD.

Typically, an arrangement pitch of the detecting elements in the FPD is not identical to an arrangement pitch of the metallic foils in the X-ray grid. Consequently, a moiré occurring from interference between the both pitches appears in the fluoroscopic X-ray image. Thus, in order to remove the moiré, the conventional X-ray imaging equipment performs image reconstruction by conducting frequency analysis of an image and removing frequency components of the moiré.

The detecting elements may occur on the detection surface of the FPD that fail to detect X-rays due to defects in a semiconductor device. Such defect sometimes occurs from failure in a gate drive or a read-out transistor, and thus all the detecting elements arranged in series are unable to perform detection. As a result, a straight line having aligned white or black defective pixels appears in the fluoroscopic X-ray image. When the foregoing calculation for removing the moiré is performed to the fluoroscopic X-ray image having such straight line, the defective pixels cause disturbance in regularity of the moiré pattern. In the image after the calculation, there appear the straight line having arranged defective pixels and a ghost with the straight line exuding and spreading in a moiré arrangement direction. As a result, visibility of the fluoroscopic X-ray image is to be degraded.

Methods of processing images that are intended to solve such problems include a method of complementing defective pixels in advance, which is disclosed, for example, in Patent Literature 1. Specifically, in the conventional image processing method, as shown in FIG. 10(a), a defective region L is complemented with reference to a pixel value of the pixels adjacent to the defective region L. In addition, when the defective range L is arranged in a direction where a dark range region D in the moiré extends, a moiré that must have appeared in the defective region L deviates from and the moiré that appears in the pixels adjacent to this. Consequently, an approach shown in FIG. 10(a) cannot be adopted. Alternatively, as shown in FIG. 10(b), a statistical process is performed from right and left pixels E1 and E2 to the regions adjacent to the defective pixels a to be complemented that are arranged in series in the mere arrangement direction (x-direction), for calculating the most proper pixel value and substituting the value into the defective region L.

[Patent Literature 1]
Japanese Patent Publication No. 2002-330341

DISCLOSURE OF THE INVENTION

Problem to be Solved by the Invention

According to the conventional method, however, when the defective region L extends in the moiré extending, direction (y-direction) (see FIG. 10(b)), the defective region L is complemented regardless of the regularity of the moiré pattern. Finally, complement of the defective pixels causes disturbance in regularity of the moiré pattern. With the conventional configuration, a statistical process is performed from right and left pixels E1 and E2 to the defective region L, which comprises defective pixels a arranged in series in the y-direction, for calculating the most proper pixel value. In the statistical process, the pixel values from the right and left pixels E1 and E2 to the defective region L are examined to perform maximum likelihood estimation that estimates the most proper pixel value for complement to the defective region L. The maximum likelihood estimation is simply performed based on pixel value variations. Of course, an order of the pixels is not under consideration, and regularity of the moiré pattern is never concerned with a processed image.

Such problems are shown in FIG. 11. For simplification, it is assumed that the fluoroscopic X-ray image appears no image of the subject but a moiré only, and that the unprocessed fluoroscopic X-ray image originally has a linear defective region L extending in a position where the dark region D of the moiré appears as shown in FIG. 11(a). Here, the pixel value of the dark region D is to be the most proper in the pixel values for complement to the defective region L. However, the pixel value determined by the maximum likelihood estimation with the conventional configuration is not always to be a pixel value of the dark region D. Consequently, as shown in FIG. 11(b), the processed image differs in pixel value between the dark region D and the region L1 where the defective pixel is complemented, which leads to disturbance in regularity of the moiré pattern. For instance, when frequency analysis is conducted to the image where the defective pixel is complemented for removing the moiré, there appear a trace L2 of the defective pixels and a ghost L3 with the trace exuding and spreading in the moiré arrangement direction, as shown in FIG. 11(c), due to disturbance in regularity of the moiré pattern.

This invention has been made regarding to the state of the art noted above, and its object is to provide a method of removing a moiré in a fluoroscopic X-ray image that preliminarily complements defective pixels with no disturbance in regularity of a moiré pattern to ensure that no trace of the defective pixels and no ghost thereof create as well as X-ray imaging equipment using therewith, even when the fluoroscopic X-ray image contains the defective pixels.

Means for Solving the Problem

The invention is configured as stated below in order to achieve the above object. The invention according to claim 1 is a method of removing a moiré in a fluoroscopic X-ray image. The method includes a moiré frequency derivation step for determining frequency of the moiré that appears in the fluoroscopic X-ray image, a defective pixel preliminary complement step for complementing a defective pixel with reference to a pixel apart from the defective pixel by an integral multiple of one cycle of the moiré, thereby forming a first intermediate image, a moiré removal step for conducting frequency analysis of the first intermediate image and remove the moiré that appears in the first intermediate image, thereby forming a second intermediate image, an image smoothing step for performing an image smoothing process to the first intermediate image, thereby forming a third intermediate image, and a defective pixel recomplement step for recomplementing the defective pixel by superimposing the second intermediate image on the third intermediate image.

Operation and Effect

According to this invention, the defective pixel may be complemented with no disturbance in regularity of the moiré pattern. In the defective pixel preliminary complement step of this invention, the defective pixel is complemented with reference to the pixel apart from the defective pixel by an integral multiple of one cycle of the moiré. Consequently, the pixel to be referred has a moiré pattern that should appear in the defective pixel. For instance, when the defective pixel extends in a position where the dark region of the moiré appears, the pixel to be referred is the dark region of the moiré. Similarly, when the defective pixel extends in a position where the light region of the moiré appears, the pixel to be referred is certainly the light region of the moiré. In addition, when the defective pixel extends in a position where the light region of the moiré appears, the pixel to be referred is certainly the light region of the moiré. As noted above, complement of the defective pixel according to this invention never leads to disturbance in regularity of the moiré. Therefore, there appears no trace of the defective pixels and no ghost with the trace exuding and spreading in the moiré arrangement direction in removing the moiré that appears in the first intermediate image.

Moreover, with the foregoing construction, it is ensured that the defective pixel is complemented even when the pixel adjacent to the defective pixel is a defective pixel. Specifically, a pixel suitable for complement of the defective pixel is obtained by performing a smoothing process to the image having the defective pixel with the preliminary complement performed thereto. Thus, it is ensured that a pixel exists suitable for complement of every defective pixel even when the pixel adjacent to the defective pixel is a defective pixel. That is, with the foregoing construction, a pixel suitable for complement of the defective pixel is determined using not only the pixel adjacent to the defective pixel but also the pixel there around. Accordingly, although a group of the defective pixels formed of the continued defective pixels that appears in the fluoroscopic Xray image has a more complicated shape, a processed image may be provided having the moiré that is removed therefrom with the defective pixel certainly complemented.

Moreover, every pixel suitable for complement of the defective pixel belongs to the third intermediate image. Thus, even when there are two or more defective pixels apart from one after another, complement of the defective pixels may readily be completed by merely superimposing the second intermediate image with the moiré removed therefrom on the third intermediate image. Furthermore, the third intermediate image is formed of the first intermediate image in which the defective pixel is merely preliminarily complemented to an original image with no frequency filter applied thereto. In other words, the third intermediate image is formed of an image that still has a component of frequency same as frequency of the moiré. Therefore, the third intermediate image is faithful to the original image. When a defective pixel is recomplemented using this, a processed image may be provided that exactly shows the original image.

The image smoothing process in the foregoing image smoothing step is a matrix operation using a given matrix. It is more preferable that the matrix has rows of a pixel number for one cycle of the moiré or more.

Operation and Effect

With the foregoing construction, the moiré may be removed from the third intermediate image. That is, the image smoothing process of this invention is a matrix operation. The number of rows in the matrix is a pixel number for one cycle of the moiré or more. The image smoothing may be performed using such matrix while the light region and the dark region are cancelled to each other. Accordingly, the moiré is removed from the third intermediate image. Here, the image smoothing process is also effective to the defective pixels all having adjacent defective pixels.

It is also preferable to include the a moiré frequency derivation step for determining frequency of the moiré that appears in the foregoing fluoroscopic X-ray image, a defective pixel preliminary complement step for complementing a defective pixel with reference to a pixel apart from the defective pixel by an integral multiple of one cycle of the moiré, thereby forming a first intermediate image, a moiré removal step for conducting frequency analysis of the first intermediate image and remove the moiré that appears in the first intermediate image, thereby forming a second intermediate image, and a defective pixel recomplement step for complementing a further complemented defective pixel with reference to a pixel adjacent to the defective pixel in the second intermediate image that is complemented in the defective pixel preliminary complement step.

Operation and Effect

According to this invention, the defective pixel may be complemented with no disturbance in regularity of the moiré pattern. In the defective pixel preliminary complement step of this invention, the defective pixel is complemented with reference to the pixel apart from the defective pixel by an integral multiple of one cycle of the moiré. Consequently, the pixel to be referred has a moiré pattern that should appear in the defective pixel. For instance, when the defective pixel extends in a position where the dark region of the moiré appears, the pixel to be referred is the dark region of the moiré. In addition, when the defective pixel extends in a position where the light region of the moiré appears, the pixel to be referred is certainly the light region of the moiré. That is, with the foregoing construction, complement of the defective pixel never leads to disturbance in regularity of the moiré. Therefore, there appears no trace of the defective pixels and no ghost with the trace exuding and spreading in the moiré arrangement direction in removing the moiré that appears in the first intermediate image.

Moreover, with the foregoing construction, the complemented defective pixel is recomplemented with reference to the pixel adjacent to the defective pixel in the second intermediate image. Here, the second intermediate image is an image in which the moiré is removed from the first intermediate image having a reproduced moiré pattern that should appear in the defective pixel. Consequently, the second intermediate image is not under an influence of the moiré. However, considering that the complemented defective pixel in the second intermediate image has a pixel value replaced with reference to the pixels apart therefrom, the image of the subject that falls on the complemented defective pixel differs from the image of the subject that should fall on the defective pixel. Even so, according to the foregoing construction, the image of the subject that should fall on the complement defective pixel g is reproduced as much as possible with reference to the pixel adjacent to the complement defective pixel. Therefore, the fluoroscopic X-ray image formed with the foregoing construction is suitable for diagnosis.

Moreover, X-ray imaging equipment using the foregoing method of removing the moiré in the fluoroscopic X-ray image preferably includes an X-ray source that emits X-ray beams, an X-ray detection device that detects the X-ray beams, an X-ray grid arranged in a position between the X-ray detection device and the X-ray source that removes scattered X-rays, a defective pixel preliminary complement device that performs the defective pixel preliminary complement step, a moiré removal device that perform the moiré removal step, an image smoothing device that performs the image smoothing step, and a defective pixel recomplement device that performs the defective pixel recomplement step.

Moreover, the foregoing X-ray imaging equipment preferably includes an X-ray source that emits X-ray beams, an X ray detection device that detects the X-ray beams, an X-ray grid arranged in a position between the X-ray detection device and the X-ray source that removes scattered X-rays, a defective pixel preliminary complement device that performs the defective pixel preliminary complement step, a moiré removal device that perform the moiré removal step, and a defective pixel recomplement device that performs the defective pixel recomplement step.

The specification herein also describes the invention concerning the following radiological imaging equipment. That is, X-ray imaging equipment includes (A) an X-ray source that emits X-ray beams, (B) an X-ray detection device that detects the X-ray beams, (C) an X-ray grid arranged in a position between the X-ray detection device and the X-ray source that removes scattered X-rays, (D) a moiré frequency derivation device that determines frequency of the moiré that appears in the fluoroscopic X-ray image, (E) a defective pixel preliminary complement device that complements a defective pixel with reference to a pixel apart from the defective pixel by an integral multiple of one cycle of the moiré, thereby forming a first intermediate image, (F) a moiré removal device that conducts frequency analysis of the first intermediate image and removes the moiré that appears in the first intermediate image, thereby forming a second intermediate image, (G) an image smoothing device that performs an image smoothing process to the first intermediate image, thereby forming a third intermediate image, and (H) a first defective pixel recomplement device that recomplements the defective pixel by superimposing the second intermediate image on the third intermediate image.

The image smoothing process performed by the foregoing image smoothing device is a matrix operation using a given matrix. It is more preferable that the matrix has rows of a pixel number for one cycle of the moiré or more.

In addition, the specification herein also describes the invention concerning the following radiological imaging equipment. That is, X-ray imaging equipment includes (A) an X-ray source that emits X-ray beams, (B) an X ray detection device that detects the X-ray beams, (C) an X-ray grid arranged in a position between the X-ray detection device and the X-ray source that removes scattered X-rays, (D) a moiré frequency derivation device that determines frequency of the moiré that appears in the fluoroscopic X-ray image, (E) a defective pixel preliminary complement device that complements a defective pixel with reference to a pixel apart from the defective pixel by an integral multiple of one cycle of the moiré, thereby forming a first intermediate image, (F) a moiré removal device that conducts frequency analysis of the first intermediate image and removes the moiré that appears in the first intermediate image, thereby forming a second intermediate image, and (I) a second defective pixel recomplement device that recomplements the preliminary complement pixel of the first intermediate image by replacing a pixel value of the preliminary complement pixel belonging to the first intermediate image that is preliminary complemented with a pixel value of the adjacent pixel that is adjacent to a pixel in the same position as the preliminary complement pixel in the second intermediate image.

According to the foregoing construction, even when the X-ray detection device has the defective pixel, the X-ray imaging equipment that forms an X-ray radiological image suitable for diagnosis may be provided that ensures complement of the defective pixel while suppressing a ghost with the defective pixel exuding and spreading. The foregoing construction has the X-ray grid that removes scattered X-rays. Thus, the X-ray detection device detects X-rays with scattered X-rays removed therefrom. Consequently, finally obtained is a higher contrast fluoroscopic X-ray image. In addition, the foregoing construction has the moiré removal device. Thus, the moiré is removed from the fluoroscopic X-ray image. Moreover, the foregoing construction has the defective pixel preliminary complement device, which results in reproduction of the regularity in the moiré pattern in the defective pixel. Moreover, the foregoing construction has the defective pixel recomplement device, whereby the defective pixel varies so as to have a more proper pixel value. As mentioned above, the foregoing construction may provide X-ray imaging equipment that forms an X-ray radiological image suitable for diagnosis that ensures complement of the defective pixel while suppressing a ghost with the defective pixel exuding and spreading.

Effect of the Invention

According to this invention, the defective pixel is complemented with no disturbance in regularity of the moiré pattern. In the defective pixel preliminary complement step of this invention, the defective pixel is complemented with reference to the pixel apart from the defective pixel by an integral multiple of one cycle of the moiré. Consequently, the pixel to be referred has a moiré pattern that should appear in the defective pixel. That is, according to this invention, it is ensured that the moiré is removed in advance from an image in which both of the moiré and the defective pixel are superimposed. Accordingly, the complement is just performed to the defective pixel in the subsequent imaging processes. In other words, in this invention, removal of the moiré and replacement of the defective pixel (recomplement in this invention) are performed, in turn, to the image in which both of the defective pixel and the moiré are superimposed. Therefore, replacement of the defective pixel results in no disturbance in regularity of the moiré pattern, and no trace of the defective pixels and no ghost with the trace exuding and spreading on the finally formed fluoroscopic X-ray image.

BRIEF DESCRIPTION OF THE DRAWINGS

FIG. 3 is a flow chart showing operations according to Embodiment 1.

FIG. 4 is a schematic view of the fluoroscopic X-ray image according to Embodiment 1.

FIG. 7 is an explanatory view showing an image process according to Embodiment 2.

FIG. 9 is a schematic view showing a construction of one modification according to this invention.

FIG. 10 is a schematic view showing a conventional method of removing a moiré in a fluoroscopic X-ray image.

FIG. 11 is a schematic view showing the conventional method of removing the moiré in the fluoroscopic X-ray image.

DESCRIPTION OF REFERENCES 1 moiré frequency derivation section
  (moiré frequency derivation device)
2 defective pixel preliminary complement section
  (defective pixel preliminary complement device)
3 moiré removal section (moiré removal device)
4 image smoothing section (image smoothing device)
5 first defective pixel recomplement section
  (first defective pixel recomplement device)
24 second defective pixel recomplement section
  (second defective pixel recomplement device)
P1 preliminary complement image (first intermediate image)
P2 moiré removed image (second intermediate image)
P3 smoothed image (third intermediate image)

BEST MODE FOR CARRYING OUT THE INVENTION

Description will be given, with reference to the drawings, to one embodiment concerning a method of removing a moiré in a fluoroscopic X-ray image according to this invention and to one embodiment of X-ray imaging equipment using thereof.

Embodiment 1

Figure 1:
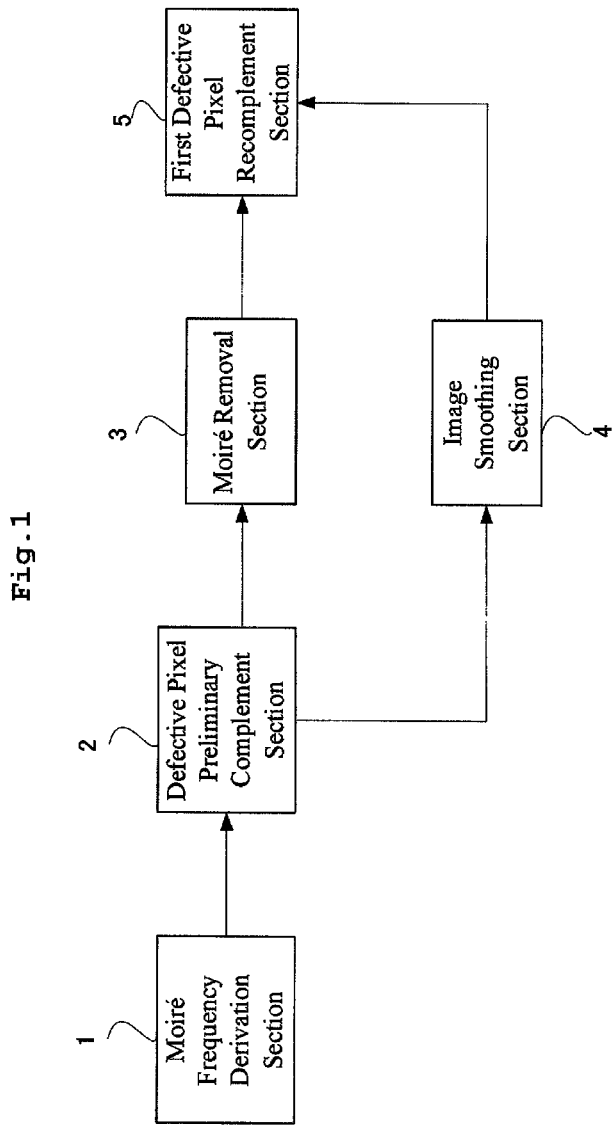
FIG. 1 is a functional block diagram showing a method of removing a moiré in a fluoroscopic X-ray image according to Embodiment 1.

FIG. 1 is a functional block diagram showing a method of removing a moiré in a fluoroscopic X-ray image according to Embodiment 1. As shown in FIG. 1, in order to remove a moiré with the method according to Embodiment 1, included are a moiré frequency derivation section 1 that determines frequency of the moiré from an original image P0, a defective pixel preliminary complement section 2 that complements a defective pixel from a pixel apart from the defective pixel by an integral multiple of one cycle of the moiré, thereby forming a preliminary complement image P1, a moiré removal section 3 that removes the moiré appearing in the preliminary complement image P1, thereby forming a moiré removed image P2, an image smoothing section 4 that performs an image smoothing process to the preliminary complement image P1, thereby forming a smoothed image P3, and a first defective pixel recomplement section 5 that recomplements the defective pixel by superimposing the moiré removed image P2 on the smoothed image P3. Here, the preliminary complement image P1, the moiré removed image P2, and the smoothed image P3 of Embodiment 1 correspond to the first intermediate image, the second intermediate image, and the third intermediate image, respectively, in this invention. Moreover, the moiré frequency derivation section corresponds to the moiré frequency derivation device in this invention. The defective pixel preliminary complement section corresponds to the defective pixel preliminary complement device in this invention. The moiré removal section corresponds to the moiré removal device in this invention. The image smoothing section corresponds to the image smoothing device in this invention. The first defective pixel recomplement section corresponds to the first defective pixel recomplement device in this invention.

Figure 2:
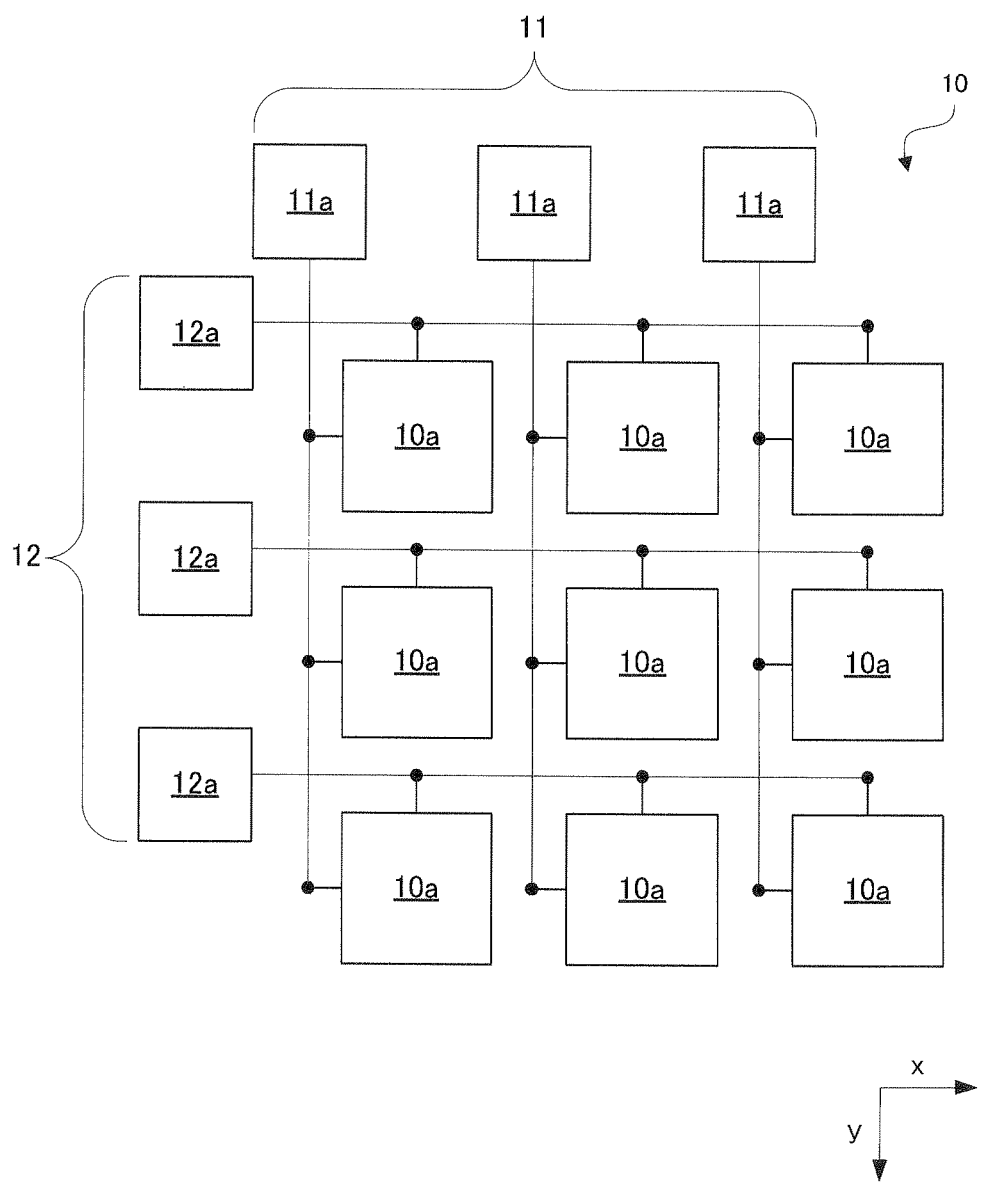
FIG. 2 is an explanatory view showing a configuration of an FPD according to Embodiment 1.

Next, description will be given to a defective pixel according to Embodiment 1. FIG. 2 is an explanatory view showing a configuration of an FPD according to Embodiment 1. As shown in FIG. 2, an FPD that detects X-rays has X-ray detecting elements arranged in matrix, a gate drive array 11 on a side end of the detecting elements in matrix, and an amplifier array 12. A defective pixel occurs when either of these does not operate completely. For instant, when failure occurs in one of gate drive elements 11a that constitute the gate drive array 11, and none of X-ray detecting elements 10a operates that is driven with the fault gate drive components 11a, a black straight line appears in the fluoroscopic X-ray image regardless of an object to be imaged. That is because the gate drive elements 11a in the FPD 10 drive en bloc the X-ray detecting elements 10a in series.

Now, description will be given to a moiré according to Embodiment 1. Typically, examples of X-ray imaging equipment that take fluoroscopic X-ray images of a subject includes one in which an X-ray source irradiates the subject with X-ray beams in a cone shape, and the FPD 10 detects transmission X-rays that transmit through the subject. In such X-ray imaging equipment, when X-rays transmit through the subject, X-rays scatter in the subject to enter into the FPD 10, which leads to which leads to a lower contrast fluoroscopic X-ray image of the subject. The X-ray grid is provided that absorbs scattered X-rays so as to cover an X-ray detection surface of the FPD 10 for prevention of the scattered X-rays from entering into the FPD 10.

Here, the FPD 10 has multiple X-ray detecting elements 10a of semiconductor type arranged in matrix. Such FPD constructs a fluoroscopic X-ray image by discretely sampling X-rays that transmits through the subject M with each of the arranged X-ray detecting elements 10a. On the other hand, the X-ray grid has two or more vanes arranged in a blind shape. When X-ray beams in a cone shape transmit through the X-ray grid, a streak shadow occurs of each vane of the X-ray grid. When seen as a whole of the X-ray grid, the shadow has a stripe X-ray shadow pattern and falls on the FPD 10 arranged under the X-ray grid. The X-ray detecting elements 10a that constitute the FPD 10 is to discretely sample the X-ray shadow pattern. The number of the X-ray shadows that fall on each of the X-ray detecting elements 10a is not constant throughout the FPD 10. That is because the arrangement pitch of the X-ray detecting elements 10a does not conform to the arrangement pitch of the X-ray shadows. Accordingly, interference stripes appear in the fluoroscopic X-ray image with the elongate dark region having a large number of shadows falling thereon and the elongate light region having a smaller number of shadows falling thereon being aligned one after another. Consequently, interference occurs between the arrangement pattern of the detecting elements of the FPD 10 and the X-ray shadow pattern with the X-ray grid to generate a moiré to appear in the fluoroscopic X-ray image. This means the moiré according to this invention. Moreover, with the construction of Embodiment 1, an image may be provided that both of the defective pixel and the moiré simultaneously appearing in the fluoroscopic X-ray image are removed therefrom.

Next, description will be given to operations of a method of removing the moiré in the fluoroscopic X-ray image according to Embodiment 1. As shown in FIG. 3(a), operations of the method of removing the moiré according to Embodiment 1 includes a moiré frequency derivation step S1 that the moiré frequency derivation section 1 performs, a defective pixel preliminary complement step S2 that the defective pixel preliminary complement section 2 performs, a moiré removal step S3 that the moiré removal section 3 performs, an image smoothing step S4 that the image smoothing section 4 performs, and a defective pixel recomplement step S5 that the first defective pixel recomplement section 5 performs. Each of operations in these steps will be described in order.

<Moiré Frequency Derivation Step S1>

FIG. 4 is a schematic view of the fluoroscopic X-ray image according to Embodiment 1. The fluoroscopic X-ray image obtained with the FPD (original image P0) includes a moiré and a defective pixel. As shown in FIG. 4(a), the moiré is the dark regions D extending in the y-direction that are arranged at equal intervals in the x-direction. Here, for expediency of explanation, it is assumed that the dark region D of the moiré has a width of one pixel and appears every four pixels in the x-direction. The width and the interval of the dark region D are not limited to this embodiment. On the other hand, a defective region La appears in the original image P0 as a black line of the defective pixels arranged in the y-direction. Here, for expediency of explanation, it is assumed that the defective region La has a width of one pixel. This invention is not limited to this embodiment. Moreover, the defective region La exists in just a position where the dark region D of the moiré appears in the original image P0. This invention is not limited to this embodiment. The defective region La appears in the actual original image P0 regardless of a phase of the moiré.

The moiré frequency derivation section 1 conducts frequency analysis on the original image P0 for deriving frequency of the moiré. The original image P0 is converted into a frequency function through conducting of the frequency analysis. In the frequency function, frequency components of the moiré are represented as a sharp peak. A maximum point in the peak is read to be given as a frequency ω of the moiré.

The dark regions D are aligned at an equal interval in the x-direction. Accordingly, it is assumed that the original image shown in FIG. 4(a) is of 13×13 pixels, five dark regions D are to appear. In the embodiment of FIG. 4(a), however, the defective region La extends in a region where the dark region D should appear. Accordingly there are dark regions D of the moiré decreased by one in number. Here, the defective region La in the region where the dark part region D should appear is mere exemplification. In this invention, the defective region La may extend in the region where the light region of the moiré should appear.

<Defective Pixel Preliminary Complement Step S2>

Next, a defective pixel is preliminarily complemented. The defective region La has an extreme pixel value. Consequently, when the moiré is removed with the defective region La remaining, a ghost of the defective region La appears in the image. Then, prior to removal of the moiré, the defective region La is replaced in advance with an adjacent pixel. Specifically, as shown in FIG. 4(b), the defective pixel a is replaced with a pixel b with reference to the pixel b that is in a same position as the defective pixel a in a direction where the moiré extends (y-direction) and apart from the defective pixel a in the arrangement direction (x-direction) by four pixels corresponding to one cycle of the moiré. As above, in the defective pixel preliminary complement step S2 according to Embodiment 1, the defective pixel is replaced with the pixel in the x-direction, whereby the preliminary complement is performed of the defective pixel. With the replacement, it is assumed that the defective region La is replaced with a preliminary complement region Lb. Let the image obtained in the step S2 be a preliminary complement image P1. Here in FIG. 4(b), complement processes to the defective pixels subsequent to the defective pixel a are not performed for emphasizing the process to the defective pixel a. Actually, the defective pixels are replaced in all regions of the original image P0. Here, four pixels correspond to the integral multiple of the moiré of one cycle according to this invention. Moreover, in this invention, the pixel belonging to the preliminary complement region Lb is defined as the preliminary complement pixel.

<Moiré Removal Step S3>

Subsequently, in the moiré removal step S3, frequency analysis is conducted to the foregoing preliminary complement image P1 to remove the moiré appearing in the preliminary complement image P1. Specifically, a filtering process is performed of removing frequency ω of the moiré with respect to the frequency function acquired through the frequency analysis to the preliminary complement image P1. Thereafter, the resultant is converted into a fluoroscopic X-ray image. Accordingly, as shown in FIG. 4(c), a moiré removed image P2 is obtained with the moiré removed therefrom. With the process, the moiré falling on the preliminary complement region Lb is removed and the preliminary complement region Lb is to be a region Lc having no moiré. Directing attention to the region Lc, the moiré is removed therefrom, but the referred pixels are spaced in accordance with the cycle of the moiré. That is, a pixel value more unsuitable for complement of the defective region La is to be used for the region Lc. Here, the pixel belonging to the region Lc corresponds to the defective pixel complemented in the defective pixel preliminary complement step in this invention. In the description hereinafter, it is called as the complemented pixel for expediency of explanation.

<Image Smoothing Step S4>

Figure 5:
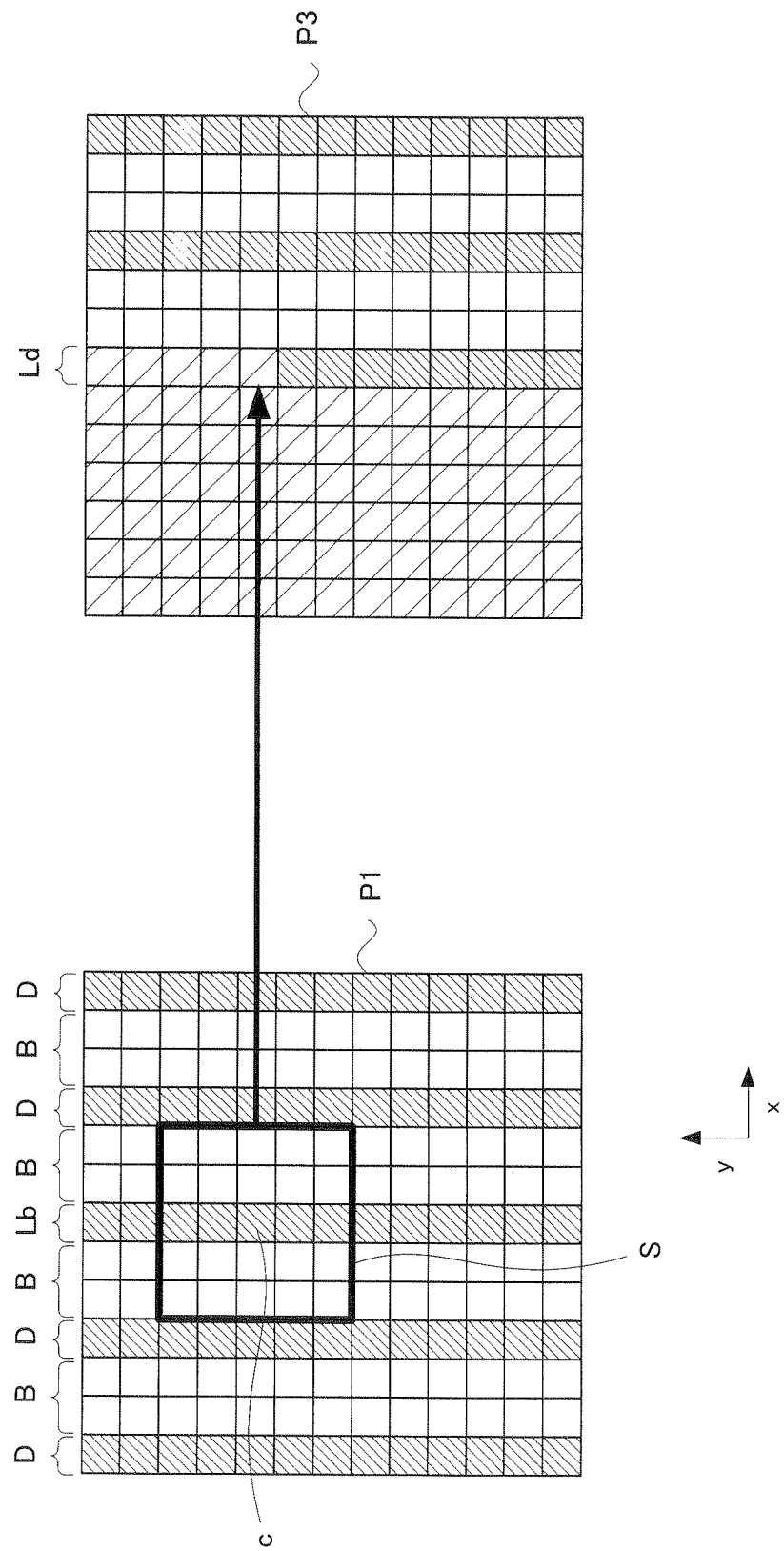
FIG. 5 is a schematic view showing an image smoothing step according to Embodiment 1.

Then, a pixel value suitable for complement of defective region La is acquired through an image data smoothing process for a more suitable pixel value in the region Lc. In the image smoothing section 4, an image data smoothing process is performed to the preliminary complement image P1 obtained in the defective pixel preliminary complement step S2, whereby a smoothed image P3 is constructed. FIG. 5 is a schematic view showing an image smoothing step according to Embodiment 1. The preliminary complement image P1 is smoothed with a convolution filter using a convolution matrix of 5×5 having a same number of rows and columns. Now, description will be given to a calculation performed with a pixel c belonging to the preliminary complement region Lb. First, a rectangular region S is prepared so as to enclose the pixel c. The rectangular region S is a square of 5×5 pixels with the pixel c as a center. That is, the rectangular region S has the same size as the convolution matrix. Specifically, the image data smoothing process with the convolution matrix is performed with respect to the pixel c using twenty-five pixels belonging to the rectangular region S.

Considering that one cycle of the moiré is of four pixels, the rectangular region S is larger than one circle of the moiré.

Consequently, assuming that a direction along the arrangement direction of the moiré patterns in the convolution matrix is determined as a row direction, the number of rows is a pixel number or more of the moiré. Moreover, the convolution filter and the convolution matrix correspond to the image data smoothing process and the matrix, respectively, in this invention.

In the image smoothing step S4, weighting is performed based on the convolution matrix to the twenty-five pixels belonging to the rectangular region S, whereby a pixel value after the process is calculated that corresponds to the pixel c. This is performed at least over all the preliminary complement regions Lb, thereby obtaining a smoothed image P3. Here, it is assumed that the preliminary complement region Lb in the preliminary complement image P1 is replaced with a smoothing process region Ld in the smoothed image P3. Here in FIG. 5, smoothing processes to the pixels subsequent to the defective pixel c are not performed for emphasizing the process to the defective pixel c. In practice, a smoothing process of the image is performed to all of the regions of the preliminary complement image P1.

No moiré is confirmed in the smoothed image P3 formed in the image smoothing step S4. That is because the convolution matrix has a size of one or more cycles of the moiré. Specifically, the rectangular region S according to Embodiment 1 is a square of 5×5 pixels, and the light region B and the dark region D of the moiré are mixed therein. Consequently, the image smoothing of the preliminary complement image P1 with the convolution filter may result in cancellation thereof to each other. Likewise, not only the pixel c but also every pixel is cancelled to one after another, and thus the moiré is removed from the smoothed image P3. In addition, the convolution filter is also effective to the defective pixels all having adjacent defective pixels. In other words, with the construction of Embodiment 1, the defective pixel is not recomplemented based on the adjacent pixel. Accordingly, although a group of the defective pixels formed of the continued defective pixels that appears in the fluoroscopic X-ray image has a more complicated shape, a processed image may be formed with the moiré removed therefrom with the defective pixel certainly complemented.

<Defective Pixel Recomplement Step S5>

Figure 6:
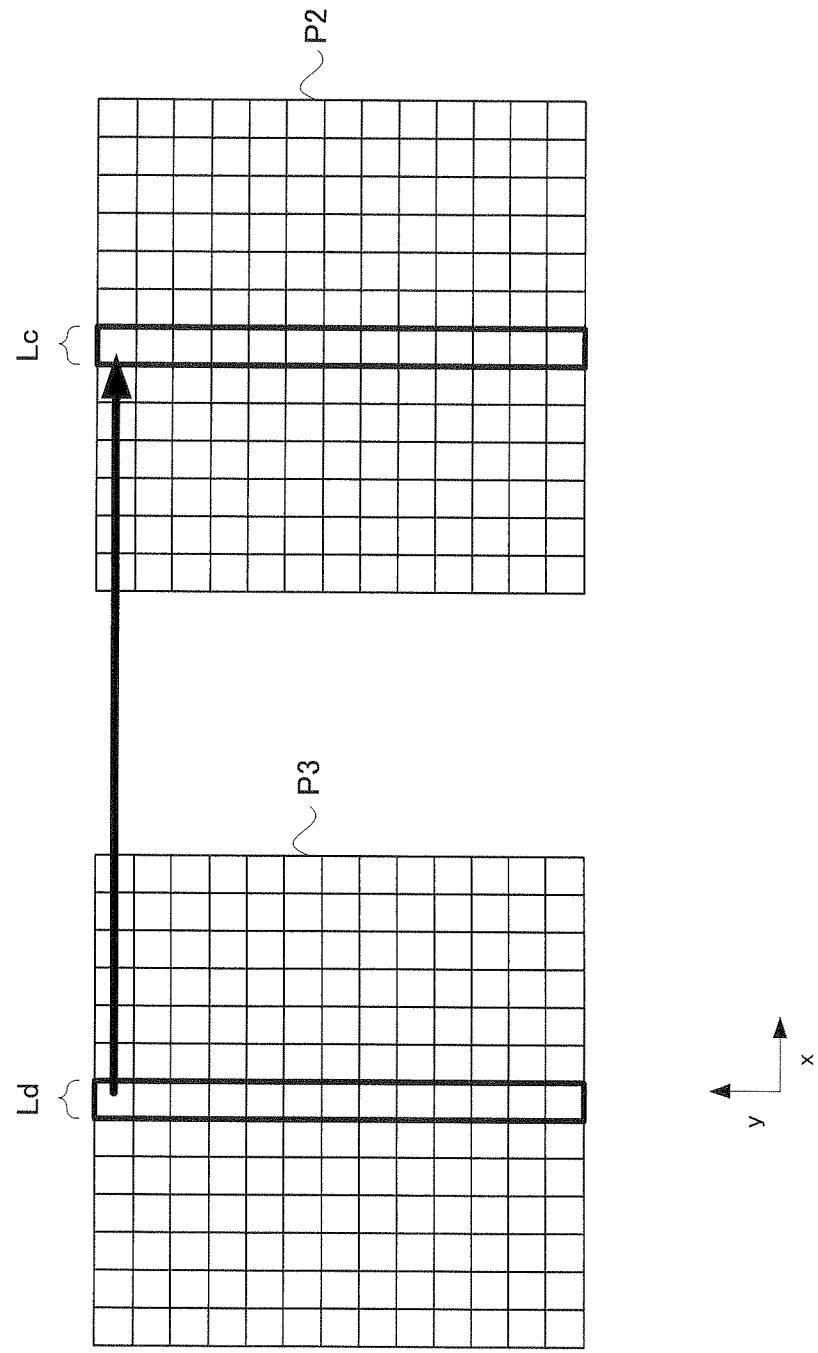
FIG. 6 is a schematic view showing a defective pixel recomplement step according to Embodiment 1.

Finally, the first defective pixel recomplement section 5 recomplements the defective pixel such that the region Lc in the moiré removed image P2 is replaced with the smoothing region Ld in the smoothed image P3. FIG. 6 is a schematic view showing a defective pixel recomplement step according to Embodiment 1. As shown in FIG. 6, the pixel value of each pixel that constitutes the region Lc in the moiré removed image P2 is replaced with a corresponding pixel value of each pixel of the smoothing region Ld in the smoothed image P3.

In comparison of the region Lc in the moiré removed image P2, the smoothing region Ld in the smoothed image P3 is more suitable for complement of the defective region La. The pixel value of the pixel apart from the defective region La is applied to the region Lc. On the other hand, the smoothing region Ld is obtained with reference to the pixels around the defective region La. Besides, the moiré is eliminated from the smoothing region Ld. Accordingly, when the region Lc in the moiré removed image P2 is replaced with the smoothing region Ld in the smoothed image P3, the fluoroscopic X-ray image may be formed in which the moiré is removed and the defective region La is completed with application of a more suitable pixel value.

With the foregoing construction according to Embodiment 1, the defective pixel La may be complemented with no disturbance in regularity of the moiré pattern. In the defective pixel preliminary complement step S2 in Embodiment 1, the defective pixel a is complemented with reference to the pixel b apart from the defective pixel La by one cycle of the moiré. Consequently, the pixel b to be referred has a moiré pattern that should appear in the defective pixel a. For instance, when the defective region La extends in a position where the dark region D of the moiré appears, the pixel to be referred is the dark region D of the moiré. In addition, when the defective region La extends in a position where the light region B of the moiré appears, the pixel to be referred is certainly the light region B of the moiré. Thus, according to Embodiment 1, complement of the defective region La never leads to disturbance in regularity of the moiré. Therefore, in the moiré removal step S3, there appears no preliminary complement region Lb as the complemented region and no ghost with the region Lb exuding and spreading in the moiré arrangement direction in removing the moiré that appears in the preliminary complement image P1.

Moreover, it is ensured that the defective pixel is complemented even when the pixel adjacent to the defective pixel is a defective pixel. Specifically, a pixel suitable for complement of the defective pixel is obtained by performing a smoothing process with the preliminary complement performed to the defective pixel. Thus, it is ensured that a pixel exists suitable for complement of every defective pixel even when the pixel adjacent to the defective pixel is a defective pixel. That is, with the foregoing construction, a pixel suitable for complement of the defective pixel is determined using not only the pixel adjacent to the defective pixel but also the pixel therearound. Accordingly, although a group of the defective pixels formed of the continued defective pixels that appears in the fluoroscopic X-ray image has a more complicated shape, a processed image may be provided having the moiré that is removed therefrom with the defective pixel certainly complemented. Moreover, every pixel suitable for complement of the defective pixel belongs to the smoothed image P3. Thus, even when there are two or more defective pixels apart from one after another, complement of the defective pixels may readily be completed by merely superimposing the moiré removed image P2 with the moiré removed therefrom on the smoothed image P3. Furthermore, the smoothed image P3 is formed of the preliminary complement image P1 in which the defective pixel is merely preliminarily complemented to an original image P0 with no frequency filter applied thereto. In other words, the smoothed image P3 is formed of an image that never loses frequency components prior to removing of the moiré. Therefore, the smoothed image P3 is faithful to the original image. When a defective pixel is recomplemented using this, a processed image may be provided that exactly shows the original image P0.

Moreover, the moiré falls on the preliminary complement region Lb, but no moiré is confirmed in the smoothed image P3 formed in the image smoothing step S4. That is because the convolution matrix has a size of one or more cycles of the moiré. The light region B and the dark region D of the moiré are mixed in a region S determined with the convolution matrix. Consequently, the image smoothing of the preliminary complement image P1 with the convolution filter may result in cancellation thereof to each other. Every pixel in the smoothed image P3 is also cancelled to one after another in such a manner, and thus the moiré is removed from the smoothed image P3.

Embodiment 2

Next, description will be given to a method of removing the moiré in the fluoroscopic X-ray image according to Embodiment 2. FIG. 7(a) is an explanatory view showing the method of removing the moiré in the fluoroscopic X-ray image according to Embodiment 2. As shown in FIG. 7(a), in order to remove a moiré with the method according to Embodiment 2, included are a moiré frequency derivation section 21 that determines frequency of the moiré from an original image P0, a defective pixel preliminary complement section 22 that complements a defective pixel with reference to a pixel apart from the defective pixel by an integral multiple of one cycle of the moiré, thereby forming a preliminary complement image P1, a moiré removal section 23 that removes the moiré appearing in the preliminary complement image P1, thereby forming a moiré removed image P2, and a second defective pixel recomplement section 24 that recomplements the complemented defective pixel with reference to a pixel in the moiré removed image P2. Here, the preliminary complement image P1 and the moiré removed image P2 of Embodiment 2 correspond to the first intermediate image and the second intermediate image, respectively, in this invention. The second defective pixel recomplement section corresponds to the second defective pixel recomplement device in this invention.

Next, description will be given to operations in the method of removing the moiré in the fluoroscopic X-ray image according to Embodiment 2. As shown in FIG. 3(b), operations in removing the moiré according to Embodiment 2 includes a moiré frequency derivation step S1 that the moiré frequency derivation section 21 performs, a defective pixel preliminary complement step S2 that the defective pixel preliminary complement section 22 performs, a moiré removal step S3 that the moiré removal section 23 performs, and a defective pixel recomplement step T4 that second defective pixel recomplement section 24 performs. Among them, steps S1 to S3 are same as those in Embodiment 1, and the explanation thereof is to be omitted.

<Defective Pixel Recomplement Step T4>

Description will be given to the defective pixel recomplement step T4 that is a characteristic step in Embodiment 2. FIG. 7(b) is a schematic view showing the defective pixel recomplement step according to Embodiment 2. As shown in FIG. 7(b), in the defective pixel recomplement step T4, an operation is performed of replacing a pixel value of a preliminary complement defective pixel g with reference to a pixel h that never belongs to the region Lc in the moiré removed image P2. Specifically, let a pixel be a pixel h that never belongs the region Lc among pixels that enclose the preliminary complement defective pixel g to be recomplemented. A pixel value of the pixel h is read out to modify a pixel value of the preliminary complement defective pixel g into this. Accordingly, a fluoroscopic X-ray image may be formed in which the preliminary complement defective pixel g is recomplemented. That is, the second defective pixel recomplement section 24 recomplements the preliminary complemented defective pixel g in the preliminary complement image P1 by replacing a pixel value of the preliminary complement defective pixel g (preliminary complement pixel) belonging to the preliminary complement image P1 with a pixel value of a pixel h that is adjacent to a pixel in the same position as the defective pixel g in the moiré removed image P2.

With the foregoing construction according to Embodiment 2, the defective pixel a may be complemented with no disturbance in regularity of the moiré pattern. In the defective pixel preliminary complement step S2 in Embodiment 2, the defective pixel a is complemented with reference to the pixel b apart from the defective pixel a by one time of the numbers of pixels for one cycle of the moiré. Consequently, the pixel b to be referred has a moiré pattern that should appear in the defective pixel a. That is, according to the construction of Embodiment 2, complement of the defective pixel a never leads to disturbance in regularity of the moiré. Therefore, there appears no trace of the defective pixels and no ghost with the trace exuding and spreading in the moiré arrangement direction in removing the moiré that appears in the preliminary complement image P1.

However, considering that the preliminary complemented defective pixel g in the moiré removed image P2 has a pixel value replaced with reference to the pixel b apart therefrom, the image of the subject that falls on the preliminary complemented defective pixel g differs from the image of the subject that should fall on the defective pixel a. Even so, according to the construction of Embodiment 2, the image of the subject that should fall on the preliminary complement defective pixel g is reproduced as much as possible with reference to the pixel h adjacent to the preliminary complement defective pixel g. Therefore, the fluoroscopic X-ray image formed with the construction of Embodiment 2 is suitable for diagnosis.

Embodiment 3

Next, description will be given, with reference to drawings, to X-ray imaging equipment using the moiré removal step described in Embodiment 1 and Embodiment 2.

Figure 8:
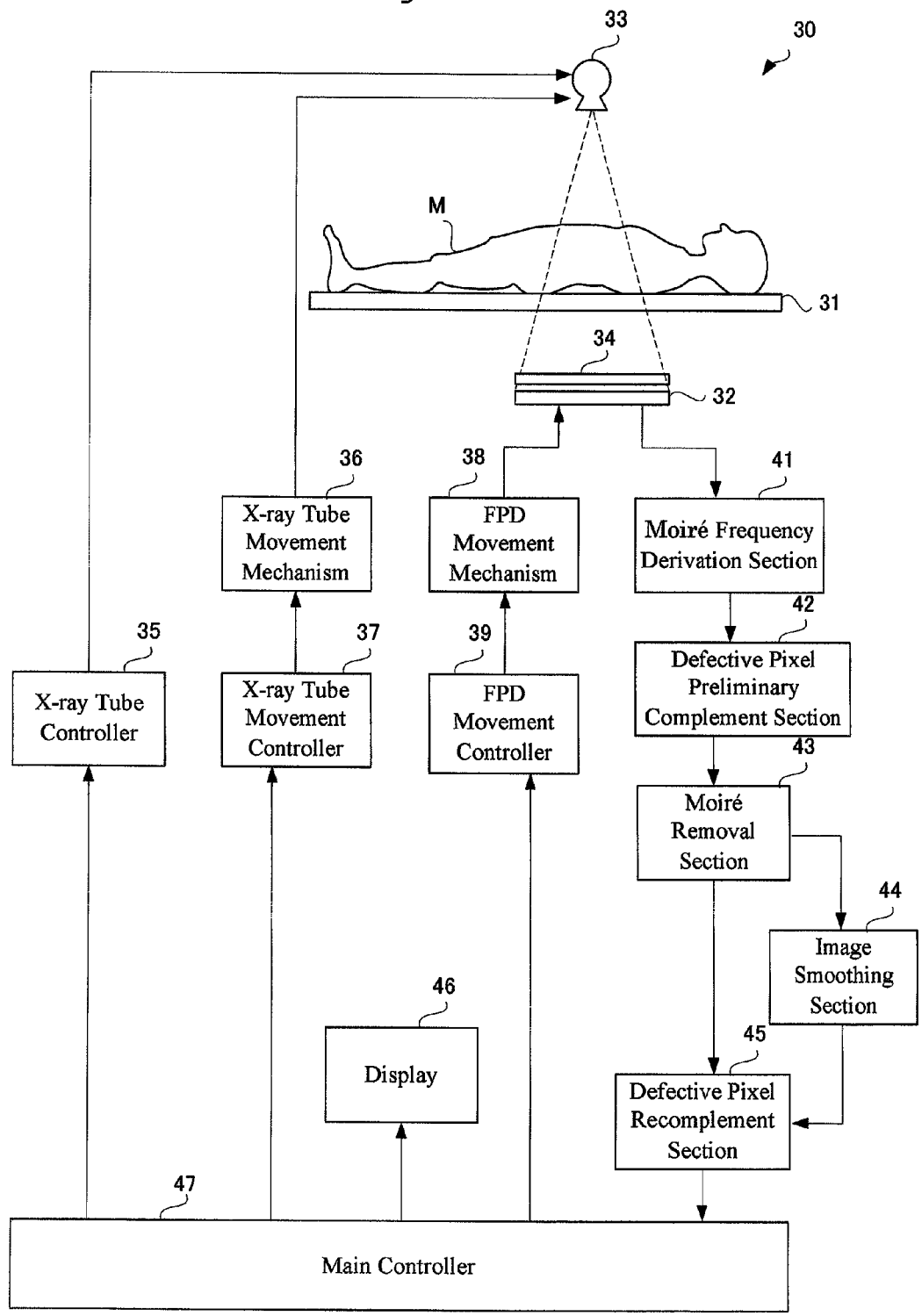
FIG. 8 is a functional block diagram showing a construction of X-ray imaging equipment according to Embodiment 3.

FIG. 8 is a functional block diagram showing a construction of the X-ray imaging equipment according to Embodiment 3. As shown in FIG. 8, included are a top board 31 that supports a subject M, an FPD 32 provided below the top board 31, an X-ray tube 33 provided over the top board for irradiating the FPD 32 with X-ray beams in a cone shape, an X-ray grid 34 arranged in a position between the FPD 32 and the X-ray tube 33 so as to cover an X-ray detecting surface of the FPD 32 for removing scattered X-rays, an X-ray tube controller 35 that controls a tube voltage in the X-ray tube 33, an X-ray tube movement mechanism 36 that moves the X-ray tube 33 and an X-ray tube movement controller 37 that controls thereof, an FPD movement mechanism 38 that moves the FPD 32 and an FPD movement controller 39 that control thereof, a moiré frequency derivation section 41 that conducts frequency analysis to an original image P0 outputted from the FPD 32, a defective pixel preliminary complement section 42 that preliminarily complements a defective pixel La contained in the original image P0, thereby forming a preliminary complement image P1, a moiré removal section 43 that removes a moiré appearing in the preliminary complement image P1, thereby forming a moiré removed image P2, a defective pixel recomplement section 45 that recomplements the complement defective pixel to the moiré removed image P2, and a display 46 that displays a fluoroscopic X-ray image. Specifically, the defective pixel recomplement section 45 is either the foregoing first defective pixel recomplement section 5 or the second defective pixel recomplement section 24.

Where the construction of Embodiment 1 is adopted, the X-ray imaging equipment 30 according to Embodiment 3 has an image smoothing section 44 that performs a smoothing process to the preliminary complement image P1, thereby forming a smoothed image P3. This construction is not always needed when the construction of Embodiment 2 is adopted.

The X-ray imaging equipment 30 also includes a main controller 47 for performing an overall control of the controllers 35, 37, and 39. The main controller 47 has a CPU, and realizes the controllers 35, 37, and 39 by executing various programs. Here, the X-ray tube 33 and the FPD 32 correspond to the X-ray source and the X-ray detection device, respectively, in this invention. In addition, the moiré frequency derivation section, the defective pixel preliminary complement section, the moiré removal section, the image smoothing section, and the defective pixel recomplement section correspond to the moiré frequency derivation device, the defective pixel preliminary complement device, the moiré removal device, the image smoothing device, and the defective pixel recomplement device, respectively.

When the X-ray imaging equipment 30 according to Embodiment 3 takes a fluoroscopic X-ray image, the subject M is firstly placed on its back on the top board 31. Thereafter, the FPD 32 and the X-ray tube 33 are moved to a position where a region of interest in the subject M is sandwiched. Then, the X-ray tube 33 is controlled as to emit X-ray beams in the cone shape. Here, the X-ray beams in the cone shape are of pulse form.

X-rays that transmit through the subject M pass through the X-ray grid 34, and then enter into the FPD 32. Consequently, a moiré appears in the original image P0 outputted by the FPD 32 that occurs from interference of between an arrangement pitch of the detecting elements in the FPD 32 and an arrangement pitch of the metallic foil in the X-ray grid 34.

The moiré is removed from the original image P0 to covert it into a fluoroscopic X-ray image suitable for diagnosis through a moiré frequency derivation step S1 that the moiré frequency derivation section 41 performs, a defective pixel preliminary complement step S2 that the defective pixel preliminary complement section 42 performs, a moiré removal step S3 that the moiré removal section 43 performs, an image smoothing step S4 that the image smoothing section 44 performs, and a defective pixel recomplement step that the defective pixel recomplement section 45 performs. The image processing has been described in detail in each of the foregoing embodiments. Thus, the explanation is to be omitted. As noted above, obtaining is completed of the fluoroscopic X-ray image with the X-ray imaging equipment that is described in Embodiment 1 and Embodiment 2 using the moiré removal step.

Where the construction of Embodiment 1 is adopted, the defective pixel recomplement section 45 operates the step S5 described in Embodiment 1. Moreover, where the construction of Embodiment 2 is adopted, the defective pixel recomplement section 45 performs the step T4 described in Embodiment 2.

As mentioned above, the construction of Embodiment 3 may provide X-ray imaging equipment 30 that forms an fluoroscopic X-ray image suitable for diagnosis that ensures complement of the defective pixel a while suppressing a ghost with the defective pixel a exuding and spreading even when the FPD 32 has the defective pixel a. Embodiment 3 has the X-ray grid 34 that removes scattered X-rays. Thus, the FPD 32 detects X-rays with scattered X-rays removed therefrom. Consequently, finally obtained is a higher contrast fluoroscopic X-ray image. In addition, the construction of Embodiment 3 has the moiré removal section 43. Thus, the moiré is removed from the fluoroscopic X-ray image. Embodiment 3 has the defective pixel preliminary complement section 42. Accordingly, regularity of the moiré pattern is reproduced in the defective pixel. Furthermore, Embodiment 3 has the defective image recomplement section 45. Accordingly, the pixel value of the defective pixel a is modified into a suitable one. As mentioned above, the construction of Embodiment 3 may provide X-ray imaging equipment 30 that forms an fluoroscopic X-ray image suitable for diagnosis that ensures complement of the defective pixel a while suppressing a ghost with the defective pixel exuding and spreading even when the FPD 32 has the defective pixel a.

This invention is not limited to the foregoing embodiments, but may be modified as follows.

(1) In the defective pixel preliminary complement step in each of the foregoing embodiments, the defective pixel is replaced with reference to the pixel that is apart from the defective pixel a by four pixels corresponding to one cycle of the moiré in the moiré arrangement direction (x-direction.) This invention is not limited to this embodiment. As shown in FIG. 9(a), reference is given to two or more pixel values of the pixels b1 and b2 apart from the defective pixel by four pixels in the x-direction, and an average value thereof may be used to the defective pixel a.

(2) In the defective pixel preliminary complement step in each of the foregoing embodiments, the pixel b that is referred in complement of the defective pixel a is in a same position as the defective pixel a in a direction where the moiré extends (y-direction.) This invention is not limited to this embodiment. As shown in FIG. 9(b), reference may be given to a pixel apart from the defective pixel a by one pixel in the moiré arrangement direction (y-direction.) Moreover, in this invention, a distance spaced in the y-direction may freely be set.

(3) In the defective pixel preliminary complement step in each of the foregoing embodiments, the pixel b that is referred in complement of the defective pixel a is apart from the defective pixel a by one cycle of the moiré in the moiré arrangement direction (x-direction.) This invention is not limited to this embodiment. For instance, the pixel may be referred that is apart from the defective pixel a by two cycles of the moiré. That is, in this invention a distance spaced in the x-direction may be an integral multiple of one cycle of the moiré.

(4) In the defective pixel recomplement step described in Embodiment 2, the preliminary complement defective pixel g is recomplemented with reference to the pixel h. This invention is not limited to this embodiment. The preliminary complement defective pixel g may be recomplemented with reference to two or more pixels adjacent to the preliminary complement defective pixel g.

INDUSTRIAL UTILITY

As described above, this invention is suitable for medical fields.

The invention claimed is:

1. A method of removing a moiré in a fluoroscopic X-ray image having both a defective pixel and the moiré appearing therein, comprising:

a moiré frequency derivation step for determining frequency of the moiré that appears in the fluoroscopic X-ray image;

a preliminary defective pixel complement step for complementing the defective pixel with reference to a pixel apart from the defective pixel by an integral multiple of one cycle of the moiré, thereby forming a first intermediate image having the defective pixel being preliminary complemented;

a moiré removal step for conducting frequency analysis of the first intermediate image having the defective pixel being preliminary complemented and remove the moiré that appears in the first intermediate image, thereby forming a second intermediate image having the moiré removed therefrom;

an image smoothing step for performing an image smoothing process to the first intermediate image having the defective pixel being preliminary complemented, thereby forming a third intermediate image to which an image smoothing process have been performed; and a final defective pixel complement step for recomplementing the defective pixel by replacing a pixel value of a pixel in a region as the defective pixel on the second intermediate image having the moiré removed therefrom with a pixel value of a pixel corresponding to the pixel on the third intermediate image.

2. The method of removing the moiré in the fluoroscopic X-ray image according to claim 1, wherein the image smoothing process in the image smoothing step is a matrix operation using a given matrix, and the matrix has rows of a pixel number for one cycle of the moiré or more.

3. A method of removing a moiré in a fluoroscopic X-ray image having both a detective pixel and the moiré appearing therein, comprising:

a moiré frequency derivation step for determining frequency of the moiré that appears in the fluoroscopic X-ray image;
   a defective pixel preliminary complement step for complementing a defective pixel with reference to a pixel apart from the defective pixel by an integral multiple of one cycle of the moiré, thereby forming a first intermediate image having the defective pixel being preliminary complemented;
   a moiré removal step for conducting frequency analysis of the first intermediate image having the defective pixel being preliminary complemented and remove the moiré that appears in the first intermediate image, thereby forming a second intermediate image having the moiré removed therefrom; and
   a defective pixel recomplement step for complementing a further complemented defective pixel with reference to a pixel adjacent to the defective pixel in the second intermediate image having the moiré removed therefrom that is complemented in the defective pixel preliminary complement step.

4. X-ray imaging equipment comprising:
   (A) an X-ray source that emits X-ray beams;
   (B) an X-ray detection device that detects the X-ray beams;
   (C) an X-ray grid arranged in a position between the X-ray detection device and the X-ray source that removes scattered X-rays;
   (D) a moiré frequency derivation device that determines frequency of the moiré in the fluoroscopic X-ray image having both a defective pixel and the moiré appearing therein;
   (E) a detective pixel preliminary complement device that complements a defective pixel with reference to a pixel apart from the defective pixel by an integral multiple of one cycle of the moiré, thereby forming a first intermediate image having the defective pixel being preliminary complemented;
   (F) a moiré removal device that conducts frequency analysis of the first intermediate image having the defective pixel being preliminary complemented and removes the moiré that appears in the first intermediate image, thereby forming a second intermediate image having the moiré removed therefrom;
   (G) an image smoothing device that performs an image smoothing process to the first intermediate image having the defective pixel being preliminary complemented, thereby forming a third intermediate image to which an image smoothing process have been performed; and
   (H) a first defective pixel recomplement device that recomplements the defective pixel by replacing a pixel value of a pixel in a region as the defective pixel on the second intermediate image having the moiré removed therefrom with a pixel value of a pixel corresponding to the pixel on the third intermediate image.

5. The X-ray imaging equipment according to claim 4, wherein, in the fluoroscopic X-ray image,
   (G1) the image smoothing process performed by the device for forming the third intermediate image is a matrix operation using a given matrix, and the matrix has rows of a pixel number for one cycle of the moiré or more.

6. X-ray imaging equipment comprising
   (A) an X-ray source that emits X-ray beams;
   (B) an X ray detection device that detects the X-ray beams;
   (C) an X-ray grid arranged in a position between the X-ray detection device and the X-ray source that removes scattered X-rays;
   (D) a moiré frequency derivation device that determines frequency of the moiré in the fluoroscopic X-ray image having both a defective pixel and the moiré appearing therein;
   (E) a defective pixel preliminary complement device that complements a defective pixel with reference to a pixel apart from the defective pixel by an integral multiple of one cycle of the moiré, thereby forming a first intermediate image having the defective pixel being preliminary complemented;
   (F) a moiré removal device that conducts frequency analysis of the first intermediate image having the defective pixel being preliminary complemented and removes the moiré that appears in the first intermediate image, thereby forming a second intermediate image having the moiré removed therefrom; and
   (I) a second defective pixel recomplement device that recomplements the preliminary complement pixel of the first intermediate image having the defective pixel being preliminary complemented by replacing a pixel value of the preliminary complement pixel belonging to the first intermediate image that is preliminary complemented with a pixel value of the adjacent pixel that is adjacent to a pixel in a same position as the preliminary complement pixel in the second intermediate image having the moiré removed therefrom.

* * * * *